United States Patent [19]

Seyl

[11] 4,060,461
[45] Nov. 29, 1977

[54] METHOD AND APPARATUS FOR CORRECTING ERROR IN CORROSION RATE MEASUREMENTS

[76] Inventor: Robert G. Seyl, 1123 Mulford St., Evanston, Ill. 60202

[21] Appl. No.: 654,854

[22] Filed: Feb. 3, 1976

Related U.S. Application Data

[63] Continuation-in-part of Ser. No. 530,870, Dec. 9, 1974, Pat. No. 3,947,329.

[51] Int. Cl.$^2$ ............................................. G01N 27/46
[52] U.S. Cl. ................................. 204/1 T; 204/195 C
[58] Field of Search ............. 204/1 C, 195 C; 324/29, 324/71 R

[56] References Cited

U.S. PATENT DOCUMENTS

| | | | |
|---|---|---|---|
| 3,694,324 | 9/1972 | Seyl | 204/1 C |
| 3,850,736 | 11/1974 | Seyl | 204/195 C |

Primary Examiner—John H. Mack
Assistant Examiner—Aaron Weisstuch
Attorney, Agent, or Firm—McWilliams & Mann

[57] ABSTRACT

Apparatus and method for correction of error in measuring accelerated and unaccelerated corrosion rates. Means included within a single device that operates through two duplicated electrodes and includes correction for IR losses of ionic conduction between said electrodes, of lead wires from said electrodes to said device, and of circuitry within said device.

10 Claims, 3 Drawing Figures

METHOD AND APPARATUS FOR CORRECTING ERROR IN CORROSION RATE MEASUREMENTS

This application is a continuation-in-part of my patent now U.S. Pat. No. 3,947,329, filed Dec. 9, 1974, issued Mar. 30, 1976, which application Ser. No. 530,870 is related to my U.S. Pat. No. 3,850,736 issued Nov. 26, 1974, filed Sept. 25, 1972, which is a division of my U.S. Pat. No. 3,694,324, issued Sept. 26, 1972 and filed Jan. 16, 1969.

This invention relates to device and method for measuring unaccelerated and accelerated corrosion rates of electronic conductors by non-gaseous ionic conductors, and more specifically is directed to a basic form of device that measures with optimized sensitivity and accuracy.

BACKGROUND OF THE INVENTION

In the measurement of accelerated corrosion rate as disclosed in my U.S. Pat. No. 3,694,324, the corrosion current $i_A$ occurring at the free electrode potential is measured first.

When current $i_A$ is measured according to my U.S. Pat. No. 3,069,332, two measured electrodes are required, usually in the form of duplicated electrodes. The polarizing DC voltage is applied to these electrodes to produce the polarizing current $i_p$ which polarizes the one electrode cathodically by the voltage $e_{pc}$ and the other electrode anodically by the voltage $e_{pa}$. When the ionic conductor resistance is negligible, the DC voltage applied to the electrodes measures the sum of $e_{pc}$ and $e_{pa}$. Then, according to my U.S. Pat. No. 3,156,631, the measured current $_p$ is converted to the corrosion current $_A$ through linear proportionality with the Direct Voltage $E_d = 0.028$ to $0.030$ volt, as $i_A = (i_p)(E_d)/(e_{pa} + e_{pc}) = (i_p)(E_d)/$(Applied DC Voltage). A second measurement of $i_A$ can be made with reversed polarity of the applied DC voltage, to average the two measurements.

Following measurements of current $i_A$, the presence or absence of accelerated corrosion is detected by applying an increment of cathodic polarizing current $i_x$ to each of the duplicated measured electrodes, through means not interfering with corrosion current measurement, while measuring polarizing current $i_p$. If current increment $i_x$ produces an increase in current $i_p$, there is no evidence of the operation of accelerated corrosion mechanism, and the rate-determining corrosion current $i_R$ is determined as, $i_R = i_A$, where $i_R$ can be applied directly through Faraday's Law of Electrolysis to convert current into rate of metal weight loss.

If current increment $i_x$ produces a decrease in current $i_p$, the presence of accelerated corrosion mechanism is indicated. Measurement is then made of change in value of current $i_p$ produced by increase in value of current $i_x$, to determine the minimum value of current $i_p$, termed $i_{pb}$, produced by the application of current $i_x$. Current $i_{pb}$ is converted to bounding corrosion current $i_B$ through the Direct Voltage $E_d$, as described above. The accelerated corrosion mechanism then measures corrosion rate as, $i_R = 2.4(i_A) - i_B$. Alternatively, but generally with less accuracy, the current $i_{xb}$ at which $i_{pb}$ occurs, can be measured and taken as $i_R = i_{xb}$.

The means for cathodically polarizing each of the duplicated electrodes by current $i_x$ while not interfering with the corrosion current measurement, is through what is termed a circuit isolation device, operated as follows. The positive pole of a source of variable DC voltage is connected to an additional electrode operated as an anode. The negative pole is connected to two isolation resistors of equal ohmic value. Each of the two duplicated electrodes is connected to the negative pole through one of the isolation resistors. The ohmic value of the isolation resistors is selected to be large enough to cause an acceptable small current to flow through them from DC voltage subsequently applied or produced between the duplicated electrodes during $i_p$ measurement. This current through the isolation resistors may be taken as a maximum value of about 10% of measured corrosion current $i_A$. A meter in series with said source of variable DC voltage measures the total cathodic polarizing current $2i_x$.

In one alternative of said U.S. Pat. No. 3,694,324 the relationship between cathodic polarizing current $i_x$ and polarizing current $i_p$ of corrosion current measurement is continuously measured as current $2i_x$ is applied at a selected rate of increase, but such measurement was not always reliable when operated through isolation resistors of equal value. Method and device improvement making such continuous measurement reliable is disclosed in my application Ser. No. 530,870. Circuit means is introduced to determine difference in free electrode potential. The range through which current $2i_x$ is to be applied is determined from preceding measurement of corrosion current $i_A$. Current $2i_x$ is then applied at a selected rate of increase starting from zero, during which isolation resistor ratio is adjusted to maintain said determined difference in free electrode potential. Current $2i_x$ is then removed, and a time lapse is allowed for substantial recovery to said difference in free electrode potential. A corrosion current $i_A'$ is then measured with the isolation resistors connected but at $2i_x = 0$. The relationship between $i_p$ and $i_x$ is then continuously measured.

It is recognized that a desirable form of corrosion rate measurement device would include all measurement means and methods developed to date, with optimization made through a selection from the alternatives that they include. Optimization is directed to the relative merits of measurements made on the alternative electrode systems of one measured electrode with a reference electrode, or two measured electrodes. Measurement accuracy is further improved by extending the means for IR loss correction beyond that of ionic conduction between duplicated electrodes, to include the IR losses of the means for determining difference in free electrode potential and of the lead wires connecting the electrodes to the measurement device.

OBJECTS

The main object of this invention is a basic form of device for detecting and measuring unaccelerated and accelerated corrosion rates, operated through methods and means that substantially eliminate voltage loss errors in corrosion current and rate measurements.

Another object is the method and means for simultaneously adding voltage correction for the IR losses of ionic conduction in the corrosion cell, of lead wires from the cell to said device, and of current measurement in said device.

A further object is a full function device that is adaptable to a wide range of sophistication in design and operation, from a portable battery powered instrument to a line powered and fully automated instrument.

THE FIGURES

OPERATION OF DEVICE & METHOD

Figure 1:
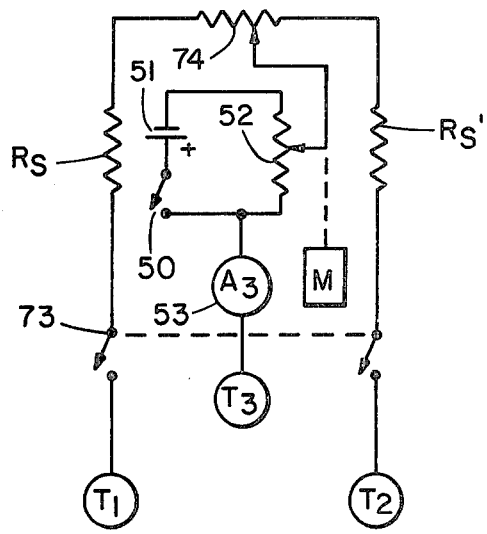
FIG. 1 is a circuit diagram of one form of circuit isolation device that can be included in the device of this invention.

The method and device of this invention are broadly directed to measurement of the corrosion rate of a system including a metal or alloy, a corrosive ionic conductor, an environment in which the corrosion operates, and the presence or absence of corrosion inhibitors or accelerators dissolved in the ionic conductor. The performance of this system is usually related to time through measurements made at selected time lapse intervals. Although particular instances can arise where measurement of corrosion rate is more desirably made on a single measured electrode, by methods disclosed in U.S. Pat. No. 3,694,324 and in my pending patent application Ser. No. 530,870, corrosion rate measurement made on duplicated measured electrodes can produce greater sensitivity and accuracy for reasons explained below.

In the measurement of corrosion current with an electrode system including a measured electrode, a reference electrode and an opposed electrode for passing the polarizing current, an error in potential measurement occurs when the measured electrode is polarized by the DC current $i_p$, of corrosion current measurement. Lines of current conduction radiate out into the ionic conductor from the surface of the measured electrode, and produce potential gradient of IR voltage drop through the ionic conductor. The spacing of the reference electrode from the measured electrode introduces some of this potential gradient in series with the half-cell potential of the reference electrode.

Since the polarization voltage measured between the measured and reference electrodes is the sum of the IR drops of the polarization resistance and of said potential gradient of ionic conduction, the measured polarization voltage will have a negative error that is transferred to the corrosion rate measurement.

This negative error increases with increase of ionic conductor resistivity and with increase of corrosion rate, while corrosion rate frequently increases with decrease of ionic conductor resistivity. In view of the broad range of corrosion system performances than can be encountered in corrosion rate measurement, it is found that the ionic conductor resistance between two electrodes can range from about 100 ohms to more than 50,000, while the measured corrosion current can range from less than one microampere to more than 2,000. The consequence is that in actual practice, the extent of this error occurring with a specific corrosion system being measured, tends to remain a vague quantity difficult to estimate, but capable of causing serious error.

The size of this error can be reduced by positioning the reference electrode in the region of least potential gradient within the ionic conductor, which calls for positioning the measured electrode between the opposed and reference electrodes.

Further attempts to reduce the size of this error through the shaping and positioning of the reference electrode are met by limitations. The error tends to be reduced by a decrease of the spacing between the measured and reference electrodes, but is limited by the spacing requirement that corrosion product build-up, occurring at least on the measured electrode, does not eventually produce contact between the measured and reference electrodes. When the electrodes are in the form of rods, a reduction in the diameter of the reference electrode tends to reduce the IR voltage gradient across this diameter, but is limited by the fragility of a wire and the length of time it can resist the corrosion. If the reference electrode area is reduced to substantially a point location, as by reference electrode conduction through the capillary tip of an insulator, the measured potential tends to become less representative of overall electrode potential and more representative of the proximity of said point location to an anodic or cathodic area of the localized or accelerated corrosion.

The selection of duplicated measured electrodes in the method and device of this patent application, operated with IR loss correction for ionic conduction, for lead wires from the electrodes to the measuring device, and for IR losses within the device, produces maximum sensitivity in the determination of difference in free electrode potential and can substantially eliminate error in polarization voltage measurement, thereby obtaining maximum accuracy in the corrosion current measurements.

Figure 2:
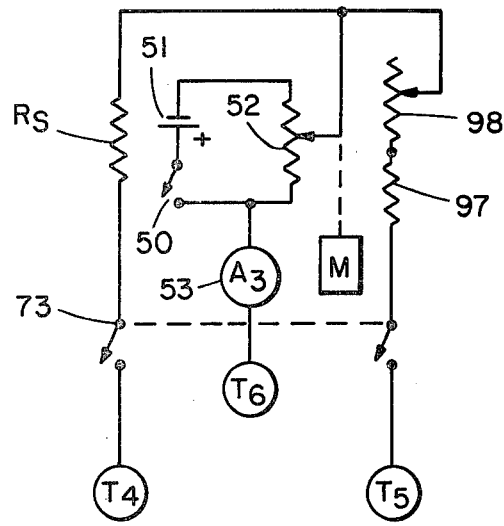
FIG. 2 is a circuit diagram of an alternative form of said circuit isolation device that can be included in the device of this invention.
Figure 3:
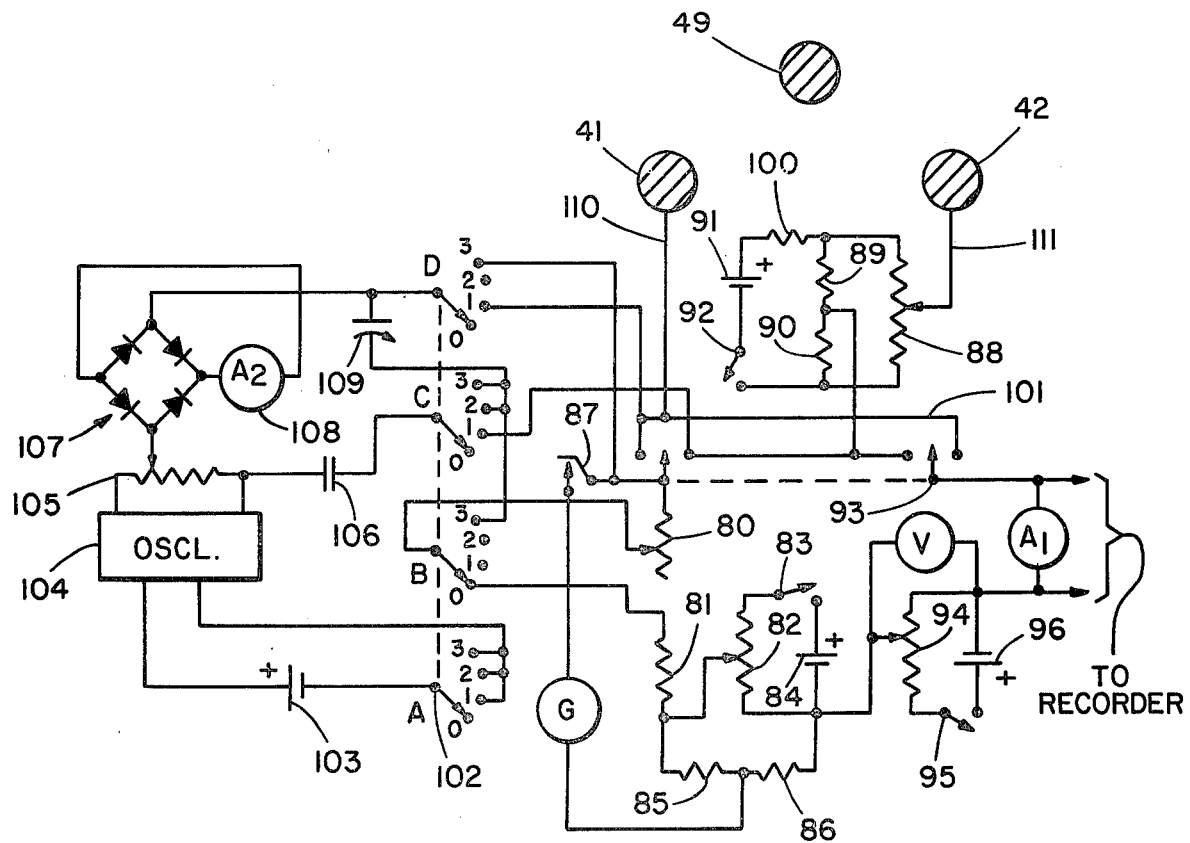
FIG. 3 is the basic circuit diagram of that portion of the device of this invention that includes the means for determining difference in free electrode potential, for application of measured polarizing DC voltage, and for measurement of the resulting polarizing current through the additional means of correcting for the IR voltage losses.

The device of this invention includes the corrosion current measurement device of FIG. 3 combined with the circuit isolation device shown in alternative form in FIGS. 1 and 2, and is connected to a corrosion probe including duplicated measured electrodes 41 and 42 and electrode 49 operated as an anode during detection and measurement of accelerated corrosion.

This device has five terminals for lead wire connection to the three electrodes of the corrosion probe, but the number of actual lead wires can be selected to be only three, or all five. The corrosion current measurement circuitry of FIG. 3 requires one lead wire from conductor 101 to electrode 41, and a second lead wire from the arm of potentiometer 88 to electrode 42. The circuit isolation device circuitry of FIG. 1 requires one lead wire from terminal $T_3$ to electrode 49. If lead wire resistance is negligible, as when the corrosion cell is located close to the measurement device, terminal $T_1$ can be connected to conductor 101 and terminal $T_2$ connected to the arm of potentimeter 88.

The corrosion cell is usually located some distance from the measurement device through necessity or convenience, and lead wire resistance can become significant. Then, since the two lead wires from FIG. 3 requires IR loss correction for polarizing current $i_p$ only, additional conductors are added to conduct current $i_x$ from terminal $T_1$ to electrode 41 and from terminal $T_2$ to electrode 42. If the device operates through the alternative circuit of FIG. 2, terminals $T_4$, $T_5$ and $T_6$ are similarly connected.

In the circuitry of FIG. 3, resistor 80 is adjusted to equal the sum $R_t$, of the resistance $R_1$ of ionic conduction between electrodes 41 and 42, the resistance $R_w$ of the lead wires connecting to electrodes 41 and 42, and the resistance $R_v$ of the circuit for subsequently determining difference in free electrode potential $\Delta E_f$. The determination of $R_t$ by alternating current measurement, whether made through the substitution method shown by way of illustration in FIG. 3 or through the alternative bridge method illustrated in U.S. Pat. No. 3,607,673 in determining $R_i$, must include determination of the distributed capacitance $C_w$, of all lead wires connected to electrodes 41 and 42.

In the determination of $R_t$ by the substitution method, capacitance $C_w$ is determined before the electrodes are immersed in the ionic conductor, and if the corrosion cell, the lead wires, and the measurement device are not moved during the progress of the corrosion, should not require further measurement. Switch 93 of FIG. 3 and switch 73 of FIG. 1 or FIG. 2 are placed in the open-circuit position shown, to disconnect other device circuitry. The four-pole, four-position switch 102 of FIG. 3 is advanced from position 0 to position 1. Pole B disconnects resistor 80 from resistor 81. Pole A connects battery 103 to oscillator 104, which delivers power to potentiometer 105 at a frequency generally selected between 400 and 1,000 Hertz. One terminal from potentiometer 105 passes through blocking condenser 106 to pole C. Said condenser blocks the flow of any DC current that may be present in subequent resistance measurement, and can have a value above about 0.5 microfarad. The arm of potentiometer 105 delivers variable voltage through full-wave rectifier 107 to pole D. Microammeter 108, generally of about 100 microampere range, measured the DC current output of rectifier 107. Pole C connects one AC output lead to the junction of resistors 89 and 90 of the circuit subsequently operated to determine difference in free electrode potential, $\Delta E_f$, and conduction continues from the arm of potentiometer 88 through the lead wire to electrode 42. Pole D connects the other AC output lead to conductor 101, where conduction continues through the lead wire to electrode 41. The arm of potentiometer 105 is adjusted to produce a measurable current through microammeter 108, which generally need not exceed about 25 microamperes. This current is produced by the distributed capacitance $C_w$ of all lead wires connected to electrodes 41 and 42. The value of this current is noted. Switch 102 is then advanced to contact position 2, which disconnects the AC voltage from the lead wires and connects it across variable condenser 109, which can have a maximum capacity of about 0.001 microfarad. Condenser 109 is then adjusted to produce the above noted value of current passing through meter 108, so that its capacity $C_w'$ is made equal to the lead wire capacitance $C_w$. Switch 102 is then returned to the 0 position.

Measurement of the corrosion currents can be made at any time selected after immersion of the electrodes into the ionic conductor. When the approximate value of corrosion current $i_A$ occurring at the free electrode potentials of the measured electrodes is not known from earlier measurement, it should be measured first for the purpose of selecting the proper ohmic range value for isolation resistor $R_r$. The resistance $R_i$ of ionic conduction between the electrodes generally changes during progress of the corrosion, so that determination of the value of $R_t$ and adjustment of resistor 80 to this value should immediately preceed the corrosion rate measurement.

In determining the value of $R_t$, switch 92 of the electrode potential equalizing circuit is closed to connect battery 91 and dropping resistor 100 across resistors 89 and 90, so that the value of $R_v$ will be that operating during subsequent corrosion current measurement. With proper design of this electrode potential equalizing circuit, the position of the arm of potentiometer 88, that delivers DC voltage within the range of only about ±0.2 volt, does not significantly alter the value of $R_v$ so that measurement can proceed to the next step. Also, said potentiometer arm is usually positioned from a preceding measurement and may require little further adjustment. With switches 93 and 73 still in the open position, switch 102 of the resistance measuring circuit is turned from position 0 to position 1, connecting one lead of the AC voltage to the wire 110 leading to electrode 41 and connecting the other lead of the AC voltage to the electrode potential equalizing circuit through which conduction continues through lead wire 111 to electrode 42. Potentiometer 105 is adjusted to produce a selected value of current on meter 108, such as about 40 microamperes, and this value is noted. Switch 102 is then advanced to position 3, which connects the AC voltage across condenser 109 and across rheostat 80. The arm of rheostat 80 is then adjusted to produce on meter 108 the value of current noted above, at which time its resistance is a measure of $R_t = R_i + R_w + R_v$. Switch 102 is then returned to position 0 where arm B returns rheostat 80 to series connection with resistor 81.

Resistance 81 is made equal to the ohmic resistance of microammeter $A_1$, taking into account the current range at which the meter is operated in measuring current $i_A$. The sum of the ohmic value of resistors 80 and 81 is then equal to the total ohmic resistance that should be corrected for when a measured DC voltage is applied to the duplicated electrodes in corrosion current measurement.

The source of voltage for correcting for IR loss is delivered from potentiometer 82 after it is energized by the closing of switch 83 in series with battery 84. The voltage delivered from potentiometer 82 is applied across duplicated resistors 85 and 86, according to my U.S. Pat. No. 3,607,673. Galvanometer G is connected across the series connection of resistors 80, 81 and 85 through momentary-close switch 87. The arm of potentimeter 82 is adjusted to maintain zero current through the galvanometer during all measurements. While this can be accomplished by manual adjustment, it is more efficiently and easily handled by a null servo drive system with high resistance input connected across the series connection of ressitors 80, 81 and 85, and with output to a motor driving the arm of potentiometer 82. Then, for any current through microammeter $A_1$, either in corrosion current measurement or in the determination of $\Delta E_f$, the voltage added through resistor 85 equals the voltage loss through resistors 80 and 81. The voltage across duplicated resistor 86 then adds voltage correction for the circuit resistance represented by resistors 80 and 81.

The means for opposing difference in free electrode potential $\Delta E_f$ between the duplicated electrodes 41 and 42 at the time of measuring corrosion currents $i_A$ and $i_A'$ includes potentiometer 88 in parallel with the series connection of resistors 89 and 90 which are usually of equal ohmic value, activated by battery 91 in series with voltage dropping resistor 100 upon the closing of switch 92. The difference in the free electrode potentials, $\Delta E_f$, is determined, in that it is opposed with precision by the adjustment of the arm of potentiometer 88, but its measurement in voltage units is not required.

Switch 93, determining the polarity of the DC voltage applied in the corrosion current measurement, is turned in a direction to connect electrodes 41 and 42. Microammeter $A_1$ is thereby connected in series with the duplicated electrodes through a small span of potentiometer 94, which is of negligible ohmic resistance. Potentiometer 88 is adjusted for zero current through microammeter $A_1$. This adjustment can be made within ±0.2 microampere on a 100 microampere meter of 3,000 ohm internal resistance.

It is worth noting that consequent to substantially complete IR loss correction, $\Delta E_f$ is determined with high precision. The current of ±0.2 microampere represents a voltage across meter $A_1$ of $e = iR = \pm(2 \times 10^{-7})(3 \times 10^3) = \pm 0.0006$ volt. The theoretical voltage difference across the poles of switch 93 is much less, since all resistances of significance in the entire circuit are corrected for. Potentiometer 94, when delivering voltage $e_p = 0.020$ volt, generally passes about 30 milliamperes when connected to battery 96. That small portion of potentiometer 94 in series with microammeter $A_1$ at the time of $\Delta E_f$ determination is only $R = 0.020/0.030 = 0.6$ ohm, which is negligible. In practice, with servo drive of the arm of potentiometer 82, this nulling can be made within a ±0.0005 volt sensitivity of the servo system.

The electrodes are thereby presented at equal potential for corrosion current measurement, so that accuracy of the current measurement does not require the averaging of two current measurements made through reversal of the applied DC voltage $e_p$. Usual practice does include polarity reversal through switch 93 after each corrosion rate measurement made during progress of the corrosion, as a precautionary measure for preserving duplicating performance by the duplicated electrodes through substantially equal time of operation as an anode and as a cathode in the corrosion current measurements. The cathodic polarization of both electrodes required in measuring bounding current $i_B$, in part cathodically protects them during the measurement, and no evidence has been encountered to show that corrosion rate measurement significantly disturbs the naturally occurring corrosion rate.

Corrosion current $i_A$ is then measured by activating potentimeter 94 by the closing of switch 95 to connect battery 96. Potentiometer 94 is adjusted to deliver DC voltage $e_p$, to the duplicated measured electrodes within the range described above as measured on voltmeter V. Measurement is made when the current $i_p$ through microammeter $A_1$, initially approaches selected slow rate of change. Switch 95 is then opened to remove voltage $e_p$, and the electrodes are allowed to return to their free electrode potentials. As disclosed above, $i_A = i_p(E_d/e_p)$.

The determination of the presence or absence of accelerated corrosion through the operation of the alternative circuits of FIG. 1 or FIG. 2 starts with the requirement that the duplicated electrodes 41 and 42 are at their free electrode potentials. Generally a time lapse of about five minutes is required after removing voltage $e_p$. During the time required for return to the free electrode potentials switch 93 could be positioned to disconnect the electrodes, but there would then be not indication of when this return was attained. It is therefore preferable to leave the electrodes connected at switch 93, and to leave switches 92 and 83 closed, so that return to free electrode potentials is indicated against time by approach of the current through meter $A_1$ to zero.

The determination of the presence or absence of accelerated corrosion, and the measurement of bounding current $i_B$ when acceleration is occurring, is described through reference to FIG. 1. Operation with the alternative circuit of FIG. 2 is identical, since rheostat 98 serves the same function as that of potentiometer 74 in FIG. 1. Circuit details and principle of operation are disclosed in my pending patent application Ser. No. 530,870.

When the presence and extent of accelerated corrosion is not known from earlier measurement, the value of isolation resistors $R_s$ and $R_s'$ of FIG. 1 which are of equal ohmic value, is generally selected within a range capable of passing cathodic current $2i_x = 10 i_A$. To minimize error in corrosion current measurement introduced by current flow through the isolation resistors, the value of $R_s$ is generally selected from the largest ohmic range capable of delivering $2i_x$ with the driving force of the DC voltage represented by battery 51. In practice, this voltage can be as large as 60 volts, and $R_s$ can be as large as two megohms, depending on the qualities of lead wire and electrode insulations. The isolation resistors $R_s$ and $R_s'$ are connected by closing switch 73. Switch 93 is closed to connect electrodes 41 and 42, and said electrodes are at their free electrode potentials as shown by zero current through meter $A_1$.

The arm of potentiometer 74 is then positioned to hold the potential difference $\Delta E_f$ while current $2i_x$ is increased at a selected rate, to generally at least 50% of its full value. The arm of potentiometer 52 is started at the position of zero voltage delivery. Switch 50 is closed to apply DC voltage 51 across potentiometer 51. Power is applied to motor M, and the arm of potentiometer 74 is adjusted to hold the current through meter $A_1$ at zero. This adjustment can generally be quickly arrived at while $2i_x$ is increased to about 30% of its full value, and verified while current $2i_x$ is increased further to about 50% of its full value.

Switch 50 is then opened, the arm of potentiometer 52 is returned to its position of zero voltage delivery, and power to motor M is disconnected.

Following this adjustment of the arm of potentiometer 74, electrodes 41 and 42 are allowed to return to substantially their initial voltage difference of $\Delta E_f$, as disclosed above after measurement of current $i_A$. A total time lapse of generally from 5 to 10 minutes is required.

Measurement is next made of corrosion current $i_A'$, made with the isolation resistors connected, and it will have a value slightly greater than $i_A$, caused by the current $i_s = (e_p + i_p R_i)/(R_s + R_{78} + R_s')$.

Determination is then made of whether or not accelerated corrosion is present. While current $i_A'$ is undergoing only small rate of change, switch 50 is closed and power is applied to motor M. When current $2i_x$ causes an increase in the value of $i_p$, to the extent of about 10%, the absence of accelerated corrosion is regarded to be confirmed, and all switches of the device are opened to allow the corrosion to continue undisturbed. The rate-determining corrosion current $i_R$, can be taken as $i_R = i_A''$, or if greater precision is required, as $i_R = i_A$.

When current $2i_x$ causes a decrease in the value of $i_p$, the measurement is continued to determine the minimum value, $i_{pb}$, and may also include determination of the value $i_{xb} = 2i_x/2$ at which said minimum occurs. In general $i_p$ decreases rapidly to a hold point, and through a small further increase in $2i_x$ the value of $i_p$ may remain substantially unchanged. Further increase in $2i_x$ then initiates increase in value of $i_p$, and the extension of measurement to include this increase is regarded to constitute assurance that the minimum value of $i_p$ has been measured. The value of $i_{pb}$ is taken as the minimum value at the start of the hold region. The value of $i_{xb} = 2i_x/2$ can be similarly taken from a reading of microammeter 53. Current $i_{pb}$ is converted to bounding current $i_B = i_{pb}(E_d/e_p)$, and the rate-determining corrosion current can be taken as $i_R = 2.4(i_A') - i_B$. All switches of the device are then opened to allow the corrosion to continue undisturbed.

In general, taking $i_R = i_{xb}$ introduces a positive error related to the speed at which motor M drives the arm of potentiometer 52, due to the lag between application of current $2i_x$ and the time required for the complete cathodic polarization producible by it to develop.

The voltage $\Delta E_f$ can be noted from the position of the arm of potentiometer 88, and could be measured. It is indicative of difference in the accelerated corrosion occurring to the duplicated electrodes. When the corrosion rate approaches a steady level, this voltage tends to become small. Thereafter, a sudden large variation in the required position of the arm of potentiometer 74 is found to be caused by the adhesion of foreign material to one electrode, such as algae, and can be taken as a warning that the corrosion rate measurements are being interfered with.

Corrosion current can be converted in the measurement device by the factor, $k = E_d/e_p$, and recorded from the voltage drop across microammeter $A_1$ or alternatively from the voltage drop across resistor 81, using a potentiometric recorder with high input resistance and a time drive abscissa axis. When $i_{xb}$ is to be included in the recording, an X-Y recorder is used. Then, in the measurement of corrosion currents $i_A$ and $i_A'$, the recorder abscissa input is taken from a source of voltage increasing at a constant rate, and the recording is calibrated to a selected time scale. In measuring $i_{pb}$ and $i_{xb}$, the abscissa input is taken from microammeter 53.

The basic device of this invention can be built to meet a wide range of alternative instrumentation requirements. In a portable device for measurements to be made in the field, all power is supplied by batteries, and motor M can be driven from a spring motor or alternatively from a battery powered motor. The nulling position of the arm of potentiometer 82 can be handled manually since the measurements of corrosion currents $i_A$, $i_A'$ and $i_B$ are made upon the attainment of slow rate of change in current $i_p$. A battery powered amplifier can be included to increase the ease of observing the deflection of galvanometer G. Alternatively, the null positioning of the arm of potentiometer 82 can be automated with a battery powered amplifier and motor. A portable battery powered recorder can be connected to such instruments.

For small volume laboratory use, battery power is replaced with line power, usually at 110 volt, 60 cycle, and the DC voltages are from separate power supplies using isolated voltage step-down, rectification, filtering, and voltage regulation. The nulling through potentiometer 82 can be operated through a DC powered AC amplifier and two-phase motor.

The extent of automation found desirable is largely determined by the economics of the measurement application, which includes measurements to be made on holidays, over week ends, and during whatever attendant-free periods may develop. For laboratory and control applications, automatic nulling can be extended to include positioning of the arms of potentiometers 105, 88, and potentiometer 74 or rheostat 98. The switching sequence is programmed, with inclusion of selected time lapses for the recoveries to free electrode potentials. Completion of a rate measurement can be signaled from the increase of $i_p$ durig the application of $i_x$. Manual adjustment is made of the current range for microammeter $A_1$, of the range values for resistors $R_s$, $R_s'$, potentiometer 74, and microammeter 53, and sometimes for adjustment of the voltage across potentiometer 82 to operate with maximum stable sensitivity. These adjustments are generally made at the time of starting a series of measurements for the purpose of meeting the requirements called for by the corrosion cell being measured. The time lapse between successive corrosion rate measurements in a series can be separately programmed.

Automation can be extended to the cyclic sequential measurement of a plurality of probe locations within one corrosion system. If such cyclic sequential measurement is applied to a plurality of corrosion systems of substantially differing corrosion rates, the programming must include switching to a separate control unit for each differing corrosion system, and may require switching to correspondingly change current ranges of the recorder.

The device of this invention is additionally applicable to the art of cathodic protection, where measurement of the electrode potential and the sustained cathodic current density at which bounding current $i_B$ occurs, is regarded to be a new and fundamental engineering reference point.

| GLOSSARY OF SYMBOLS & TERMS | | |
|---|---|---|
| Symbol | Definition | Method of Determination |
| $C_w$ | Distributed capacitance of lead wires from electrodes to device | |
| $C_w'$ | $C_w' = C_w$ | By device adjustment |
| $R_i$ | Ionic conductor resistance between the duplicated measured electrodes | Measured as part of $R_t$ |
| $R_w$ | Lead wire resistance between the electrodes and the device | Measured as part of $R_t$ |
| $R_y$ | Resistance of device circuit for equalizing free electrode potentials | Measured as part of $R_t$ |
| $R_t$ | $R_t = R_i + R_w + R_y$ | Measured |
| $R_{80}$ | $R_{80} = R_t$ | By device adjustment |
| $R_{81}$ | $R_{81}$ = internal DC resistance of meter $A_1$ at range of its operation | By switching within the device |

I claim:

1. The method for adjusting the value of a variable resistor for IR loss correction in a corrosion current measuring device operating with duplicated measured electrodes in a non-gaseous ionic conductor and having a circuit for equalizing difference in free electrode potential between said electrodes, including the steps of generating an alternating current voltage selected within the frequency range of about 400 to 1,000 Hertz, delivering said AC voltage to a potentiometer for adjustment of voltage output, leading one output terminal through a full-wave rectifier with DC output to a microammeter, and to one pole of a selector switch, leading the other output terminal through a blocking condenser to another pole of said selector switch, before immersing said electrodes in said ionic conductor, connecting the DC power supply to said circuit for equalizing difference in free electrode potential to establish its operating DC resistance, advancing said selector switch from contact position zero to position one to connect one of said poles to one of said electrodes through the lead wire from said electrode, and to connect the other of said poles to the other of said electrodes through said circuit for equalizing difference in free electrode potential and through the lead wire from said other electrode, adjusting said potentiometer to produce a measured and noted value of current through said microammeter, advancing said selector switch to contact position two to connect said poles across a variable condenser, adjusting the capacity of said variable condenser to produce through said microammeter the value of current noted above, thereby determining and storing the distributed capacity $C_w$ of said lead wires, and returning said selector switch to contact position zero until later operation in resistance measurement, at a selected time after immersion of said electrodes in said ionic conductor and immediately before corrosion current measurements of corrosion rate measurement, advancing said selector switch to contact position one, adjusting said potentiometer to produce a second measured and noted value of current through said microammeter, then advancing said selector switch to position three to connect said poles to said stored capacity $C_w$ and to a variable resistor, adjusting said variable resistor to produce said second measured and noted value of current through said microammeter, and returning said selector switch to contact position zero, whereby said variable resistor is adjusted to equal the sum of ionic conductor resistance $R_i$ between said electrodes, of lead wire resistance $R_w$ connecting said electrodes to said corrosion current measuring device, and of the resistance $R_v$ of said circuit for equalizing free electrode potential between said electrodes.

2. A device for measuring unaccelerated and accelerated corrosion rates of an electronic conductor immersed in a non-gaseous ionic conductor, including an electrode probe with two duplicated electrodes positioned at uniform separation distance, a third electrode positioned at uniform equidistant separation distance from said two duplicated electrodes, a lead wire from the end of each of said electrodes, and a corrosion resistant electrical insulator holding each of said electrodes in position at the end of lead wire connection, means for variable DC voltage delivery throughout a selected voltage range that extends from zero in both plus and minus polarity, with one output terminal connected to a lead wire from one of said duplicated electrodes, a double-pole-double-throw switch with center-off position, wired for polarity reversal with one output terminal connected to the other output terminal of said means for variable DC voltage delivery and with the other output terminal connected to the lead wire from the other of said duplicated electrodes, means for ohmic resistance determination of the sum $R_t$ of ionic conductor resistance $R_i$ between said duplicated electrodes, of the resistance $R_w$ of lead wires connecting said duplicated electrodes to said device, and of the resistance $R_v$ of said means for variable DC voltage delivery, a variable resistor means, means for adjusting said variable resistor to the ohmic value of said determined resistance $R_t$, a microammeter for measuring polarizing current $i_p$, a fixed resistor of ohmic value equal to the DC resistance of said microammeter, and connected in series with said variable resistor, two resistors of equal ohmic value connected in series and connected at one end to the one end of said series connection of said variable resistor and said fixed resistor, a second means for variable DC voltage delivery connected across said two equal resistors, voltage sensing means connectable across said series connection of said variable resistor and said fixed resistor and the one of said two equal resistors that is connected to one end of said series connection, a voltage nulling means operating through said voltage sensing means to adjust said second means for variable DC voltage delivery to maintain zero voltage input to said voltage sensing means, a low ohm resistor with one end connected to the other end of said series connection of said two resistors of equal ohmic value, a DC voltage supply connectable across said low ohm resistor for applying across said resistor a selected value of polarizing voltage $e_p$ of polarity adding to that of said second means for variable DC voltage delivery, a connection of said microammeter to the other end of said low ohm resistor, in polarity to measure DC current $i_p$ flowed by said polarizing voltage $e_p$, the connection across the input terminals of said double-pole-double-throw switch of the series connection of said variable resistor, of said fixed resistor, of the series connection of said two resistors of equal ohmic value, of said low ohm resistor, and of said microammeter, switch means for turning on and off said DC voltage supply connectable across said low ohm resistor, two isolation resistors, two cathodic terminals each connected to a first end of said isolation resistors and for connection to said two duplicated electrodes, a source of DC voltage, means for variable voltage delivery connected across said source of DC voltage, a DC current indicating device connected in series with a lead from said means for variable voltage delivery, an anode terminal connected to the positive lead from said means for variable voltage delivery and for connection to said third electrode, a ratio resistor connected in series with a second end of said two isolation resistors, a connection from the negative lead of said means for variable voltage delivery to a contact arm traversable along the resistor element of said ratio resistor, and means to increase the voltage delivered from said means for variable voltage delivery at a substantially constant rate of voltage increase from zero to maximum within a time lapse range selectable from about 3 to 10 minutes by a source of motive power.

3. The device of claim 2, in which all sources of power and voltage are supplied by batteries.

4. The device of claim 3, in which said voltage sensing means is an electronic amplifier of high input resistance, and in which said voltage nulling means is an electric motor with reversible rotation actuated from the power output of said amplifier to adjust said second means for variable DC voltage delivery.

5. The device of claim 2, in which power is obtained from the commercially available power line, and the DC voltages are from separate power supplies using isolated voltage step-down, rectification, filtering, and voltage regulation.

6. The device of claim 5, in which said voltage sensing means is an electronic amplifier of high input resistance, and in which said voltage nulling means is an electric motor with reversible rotation actuated from the power output of said amplifier to adjust said second means for variable DC voltage delivery.

7. The device of claim 6, with an electronic amplifier of high input resistance switchable across said microammeter, and with the power output of said amplifier actuating the reversible rotation of an electric motor that adjusts said first means for variable DC voltage delivery to produce zero current through said microammeter.

8. The device of claim 7, in which the drive of said motor is automatically transferred to the adjustment of said contact arm traversable along the resistor element of said ratio resistor.

9. The device of claim 5, with means to detect decrease of measuring current $i_p$ during application of cathodic polarizing current $i_x$, and with control means actuated thereby.

10. The device of claim 5, with means to detect increase of measuring current $i_p$ during application of cathodic polarizing current $i_x$, and with means to turn off said device actuated thereby.

* * * * *